US010747847B2

(12) United States Patent
Ishii et al.

(10) Patent No.: US 10,747,847 B2
(45) Date of Patent: Aug. 18, 2020

(54) MEDICAL IMAGE DIAGNOSIS APPARATUS, SERVER AND CONTROL METHOD

(71) Applicant: Toshiba Medical Systems Corporation, Otawara-shi (JP)

(72) Inventors: Hideaki Ishii, Nasushiobara (JP); Manabu Hiraoka, Nasushiobara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 0 days.

(21) Appl. No.: 15/426,582

(22) Filed: Feb. 7, 2017

(65) Prior Publication Data
US 2017/0236274 A1    Aug. 17, 2017

(30) Foreign Application Priority Data

Feb. 16, 2016  (JP) ................................ 2016-027011
Feb. 1, 2017   (JP) ................................ 2017-016669

(51) Int. Cl.
*G06F 19/00*   (2018.01)
*G06K 9/00*    (2006.01)
*G16H 10/60*   (2018.01)

(52) U.S. Cl.
CPC ....... *G06F 19/321* (2013.01); *G06K 9/00892* (2013.01); *G16H 10/60* (2018.01)

(58) Field of Classification Search
CPC ......... G06T 7/0012; G06T 2207/10081; G06T 2207/10116; G06K 9/00892; G06F 19/321; G06F 19/322
See application file for complete search history.

(56) References Cited

U.S. PATENT DOCUMENTS

| 2004/0179644 | A1  | 9/2004  | Tsuyuki |
| 2008/0243759 | A1  | 10/2008 | Martin et al. |
| 2014/0364720 | A1* | 12/2014 | Darrow ................. A61B 5/748 600/410 |
| 2015/0036793 | A1* | 2/2015  | Umekawa .............. A61B 6/032 378/8 |
| 2015/0080655 | A1* | 3/2015  | Peterson ............ A61B 1/00009 600/112 |

(Continued)

FOREIGN PATENT DOCUMENTS

| JP | 2001-249997 | 9/2001  |
| JP | 2003-33443  | 2/2003  |
| JP | 2004-275440 | 10/2004 |

(Continued)

*Primary Examiner* — Ruiping Li
(74) *Attorney, Agent, or Firm* — Oblon, McClelland, Maier & Neustadt, L.L.P.

(57) ABSTRACT

According to the embodiments, a medical image diagnosis apparatus which is accessible to an external medical scanner includes processing circuitry. The processing circuitry acquires from the medical scanner medical image data by imaging a subject based on a protocol which is a predetermined imaging procedure. The processing circuitry acquires from a sensor biometric information of at least when the subject is being photographed. The processing circuitry extracts characteristic information of the subject by processing the biometric information acquired up until a previous study. The processing circuitry assists a design of a protocol for a current study based on the characteristic information of the subject.

20 Claims, 9 Drawing Sheets

(56) References Cited

U.S. PATENT DOCUMENTS

2015/0238149 A1\*   8/2015   Nitta .................... A61B 5/055
                                                    600/413

FOREIGN PATENT DOCUMENTS

| JP | 2007-7255   | 1/2007  |
| JP | 2008-229343 | 10/2008 |
| JP | 2009-153965 | 7/2009  |
| JP | 2016-123575 | 7/2016  |

\* cited by examiner

MEDICAL IMAGE DIAGNOSIS APPARATUS, SERVER AND CONTROL METHOD

CROSS-REFERENCE TO RELATED APPLICATIONS

This application is based upon and claims the benefit of priority from the Japanese Patent Applications No. 2016-027011, filed Feb. 16, 2016 and No. 2017-016669, filed Feb. 1, 2017, the entire contents of which are incorporated herein by reference.

FIELD

Embodiments of the present invention relate to a medical image diagnosis apparatus, a server, and a control method.

BACKGROUND

In most cases, protocols in the field of medicine indicate the procedures or content, etc. of studies performed using modalities such as an X-ray computed tomography (CT) device, a magnetic resonance imaging (MRI) device, or an ultrasonic image diagnosis device. Conventionally, protocols for medical studies (examinations) were created by operators with specialized knowledge. In recent years, techniques that support creating protocols by a computer (protocol editor), or create protocols automatically are known.

Protocols are preferably designed to meticulous detail in accordance with a wide variety of elements such as symptoms, clinical conditions, age, and sex of a subject. Therefore, the matter of pursuing information sharing between modalities has been discussed by transferring a protocol management function embedded in the modality to a server device. Such technique will, for example, allow imaging protocols with clinically the same meaning to be easily applied in different modalities, or to easily realize sharing or correcting the imaging protocols between technicians.

However, a technique for allowing protocols to be designed also in consideration of the characteristics of each subject has been unknown.

DETAILED DESCRIPTION

In general, according to one embodiment, according to the embodiments, a medical image diagnosis apparatus which is accessible to an external medical scanner includes processing circuitry. The processing circuitry acquires from the medical scanner medical image data by imaging a subject based on a protocol which is a predetermined imaging procedure. The processing circuitry acquires from a sensor biometric information of at least when the subject is being photographed. The processing circuitry extracts characteristic information of the subject by processing the biometric information acquired up until a previous study. The processing circuitry assists a design of a protocol for a current study based on the characteristic information of the subject.

Figure 1:
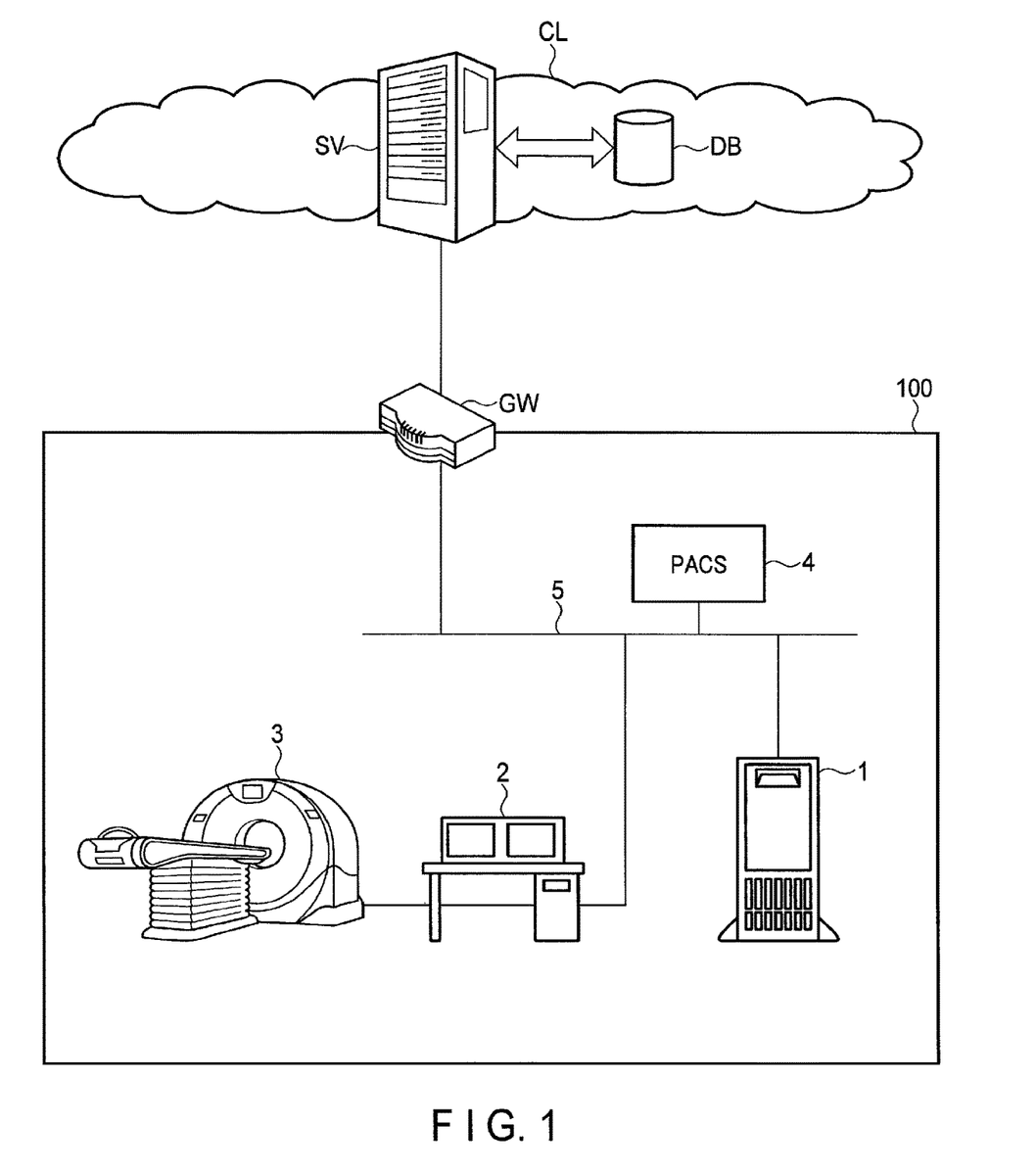
FIG. 1 shows an example of a medical information processing system to which a medical image diagnosis apparatus according to an embodiment is applicable.

FIG. 1 is a diagram showing an example of a medical information processing system to which a medical image diagnosis apparatus according to an embodiment is applicable. In FIG. 1, a hospital system 100 is communicatively connected to a cloud computing system (hereinafter, referred to as a cloud) CL via a gateway GW. The cloud CL comprises a server SV and a database DB and, for example, provides an Infrastructure as a Service (IaaS) type service.

The hospital system 100 comprises a modality 3, a console 2, and a server 1, and a Local Area Network (LAN) 5 for connecting them communicatively. The modality 3 is, for example, a medical image diagnosis apparatus such as an X-ray CT scanner, an MRI device, or an ultrasonic image diagnosis device. The modality 3 is operated by an operator via the console 2 and acquires a medical image by imaging a subject in accordance with a protocol. The acquired medical image is sent to the server 1 through the LAN 5 and stored. The medical image may be sent to the cloud CL through the gateway GW and stored in the database DB.

Figure 2:
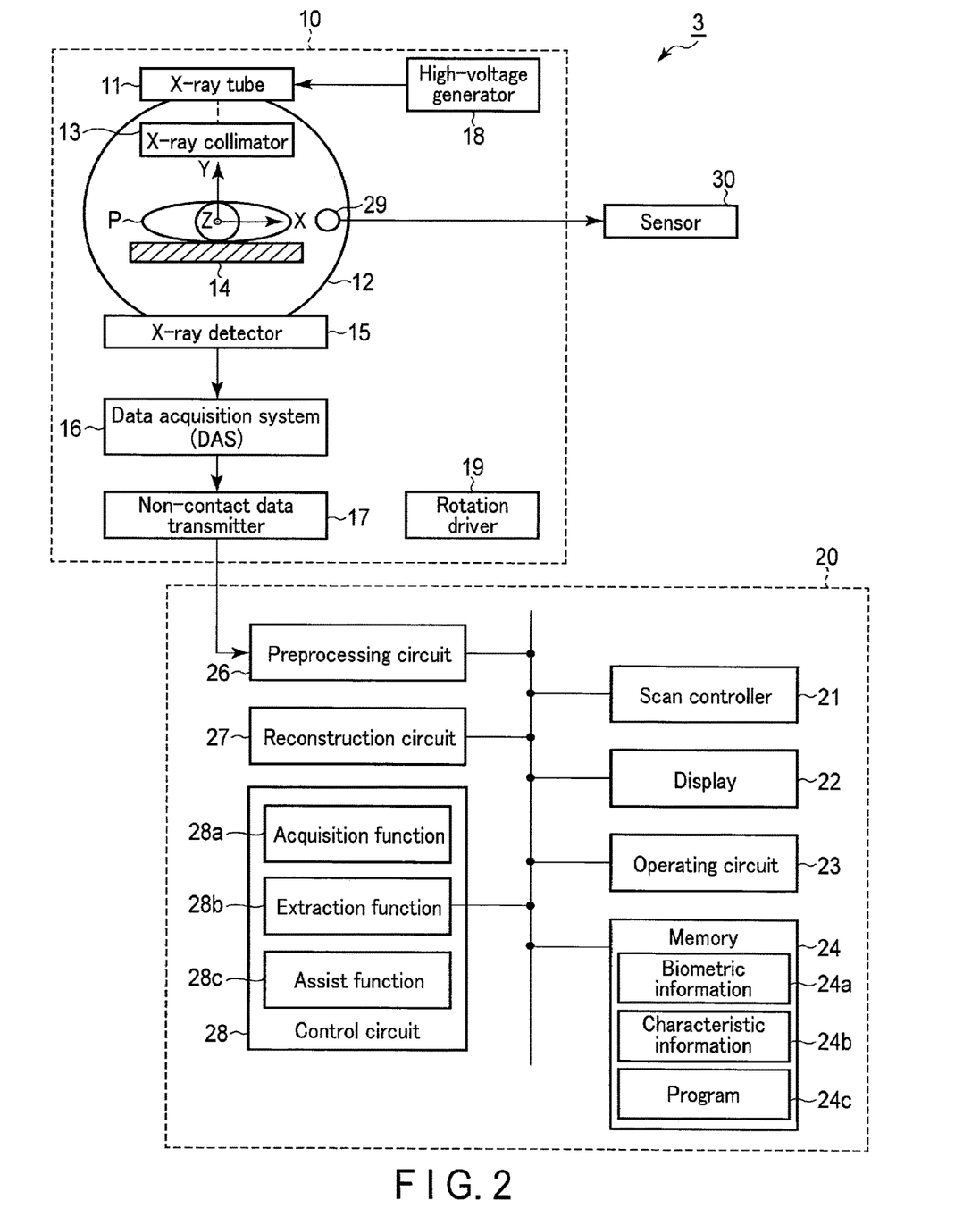
FIG. 2 shows an example of a modality 3.

FIG. 2 shows an example of the modality 3. In this embodiment, an X-ray CT scanner is assumed as the modality 3. The X-ray CT scanner comprises a scanner (gantry) 10 and a computer 20.

The scanner 10 has various mechanisms for performing a CT scan on a subject P (patient, etc.) by an X-ray. The scanner 10 executes the CT scan repeatedly under the control of a scan controller 21. In other words, the scanner 10 photographs the subject in accordance with the protocol and acquires X-ray projection data as the medical image data.

A protocol (study protocol or imaging protocol, for example), to a person skilled in the art, is understood as information expressing an imaging routine, such as, in a boarder concept, the order and the type of scanning, time intervals between scans, and scanning methods. On the other hand, in a narrower concept, a protocol indicates parameters such as a tube voltage, a tube current, an imaging angle, and an X-ray irradiation exposure within one scan. In the embodiment, the broader and the narrower protocols are both applicable. The protocol may also be understood as a predetermined imaging procedure.

Furthermore, a protocol may also indicate a set of a series of programs related to imaging, such as the purpose of imaging, an study type, an imaging method, and X-ray imaging conditions. For example, as a series of protocol groups for obtaining an image of a brain, examples such as a protocol for collecting positioning images, a protocol for shim imaging, and a protocol for imaging scan may be given.

A protocol may also indicate pulse sequence information which includes prior setting information (preset information) of imaging conditions. For example, when developing an imaging plan for an study, an operator such as a doctor or a technician reads out on a graphical user interface (GUI) a protocol group managed or provided by a modality or a server, and, while changing the preset information in accordance with need, includes it in the imaging plan.

Each protocol may include, in addition to a "Scan ID" corresponding to the name of the protocol and a "Time" which is an imaging time of the protocol, setting information of various types of imaging parameters, such as a repetition time (TR), an echo time (TE), a flip angle (FA), the number of slices (NS), a field of view (FOV), and a slice thickness (ST).

The scanner 10 supports an annular or a disk-shaped rotating frame 12 rotatably. A scan region is formed on the inner circumference side of the rotating frame 12 in which a subject P mounted on a top plate 14 is inserted. The top plate 14 is supported slidably along a longitudinal direction and a vertical direction by an unillustrated patient table.

Here, XYZ orthogonal coordinate systems are defined as follows. A Z-axis is defined as a rotating axis of the rotating frame 12. The top plate 14 is arranged so that the longitudinal direction is parallel to a Z-axial direction. An X-axis is defined as an axis in a horizontal direction, and a Y-axis is defined as an axis in a vertical direction.

The rotating frame 12 comprises an X-ray tube 11 and an X-ray detector 15. The X-ray tube 11 and the X-ray detector 15 face each other with the subject P mounted on the top plate 14 positioned therebetween. The rotating frame 12 rotates the X-ray tube 11 and the X-ray detector 15 continuously by receiving a drive signal supplied from a rotation driver 19.

The X-ray tube 11 generates an X-ray by receiving a high voltage, and by a filament current supplied from a high-voltage generator 18. An irradiation time interval of the X-ray to the subject is, for example, ten times per second. The high-voltage generator 18 applies a high voltage and supplies a tube current to the X-ray tube 11 under the control of the scan controller 21 in the computer 20. Since the tube current is changed by a change in a voltage value of the high voltage, an X-ray radiation dose may be changed.

An X-ray collimator 13 is attached on an X-ray irradiation port side of the X-ray tube 11. The X-ray collimator 13 limits the radiation field of the X-rays generated by the X-ray tube 11. Specifically, the X-ray collimator 13 comprises a plurality of diaphragm blades which are movably supported and made of a material (such as lead) that shields X-rays. By adjusting the position of the plurality of diaphragm blades, the size and the shape of the X-ray radiation field may be changed. The X-ray collimator 13 moves the diaphragm blades in response to the drive signal supplied from the scan controller 21.

The X-ray detecting section 15 detects the X-rays generated by the X-ray tube 11 and transmitted through the subject P, and generates a current signal in accordance with the intensity of the detected X-rays. A data acquisition system (DAS) 16 is connected to the X-ray detector 15.

The data acquisition system 16 collects current signals from the X-ray detector 15 under the control of the scan controller 21. The data acquisition system 16 amplifies the acquired current signals and generates digital projection data by applying digital conversion to the amplified current signals. The projection data is supplied to the computer 20 via a non-contact data transmitter 17 each time it is generated. By repeating the CT scan by the scanner 10, the projection data is generated in time series and supplied to the computer 20.

The modality 3 further comprises a sensor 30. The sensor 30 acquires biometric information of the subject P inserted inside the gantry of the scanner 10 from, for example, a probe 29 attached to the subject P. As the biometric information, the sensor 30 acquires, for example, at least one of an electrocardiograph pattern, a heart rate, or vital sign data such as respiratory information, body temperature, and amount of perspiration of the subject P.

At least the biometric information acquired during imaging of the subject P is associated with a subject identification (ID) and stored in a memory 24 of the computer 20. Alternately, the acquired biometric information is associated with a protocol and stored in the memory 24 (biometric information 24a).

The biometric information may also be transferred to the server 1 via the LAN 5 and accumulated in the database. Furthermore, the biometric information may also be accumulated in the database DB of the cloud CL via the gateway GW.

The computer 20 comprises a preprocessing circuit 26, a reconstruction circuit 27, a control circuit 28, the scan controller 21, a display 22, an operating circuit 23, and the memory 24.

The preprocessing circuit 26 applies preprocessing such as logarithmic conversion (log conversion) or sensitivity correction to the projection data (referred to as pure raw data) supplied on a real-time basis from the data acquisition system 16. The projection data to be used for image reconstruction is generated by the preprocessing. Raw data is created by applying preprocessing to the pure raw data. In the embodiment, arithmetic processing is performed by using both the raw data and the pure raw data. The pure raw data is, in essence, data of an X-ray count value detected by the X-ray detector 15. The raw data is data obtained by applying a log conversion to the pure raw data, which corresponds to a transmission length of the X-ray inside a subject.

The reconstruction circuit 27 reconstructs a CT image based on the scan data (projection data or raw data) obtained by scanning the subject P by the scanner 10.

The scan controller 21 controls the scanner 10 to perform a CT scan on the subject P by an X-ray. In other words, the scan controller 21 controls the scanner 10 in accordance with a protocol prepared for the subject P. The scan controller 21 controls the scanner 10 (specifically, the rotation driver 19, the high-voltage generator 18, the X-ray collimator 13, and the data acquisition system 16) in order to continue the scanning.

The display 22 displays the protocol on a viewer, or displays the reconstructed image or a time density curve of a contrast agent, etc. on a display device. The display device is, for example, a CRT display, a liquid crystal display, an organic EL display, or a plasma display.

The operating circuit 23 accepts various instructions and information inputs from an operator. For example, the operating circuit 23 inputs a setting position of a Region of Interest (ROI) via an input device by a user. The input device is, for example, a keyboard, a mouse, or a switch. The operating circuit 23 is, for example, also capable of giving instructions to the device to display the protocol on the viewer, or of being used to edit the displayed protocol.

The memory 24 is a memory such as a Random Access Memory (RAM) or a Read Only Memory (ROM), or a storage device such as a Hard Disk Drive (HDD). Other than a magnetic disc, a magnetic optical disc or an optical disc such as a Compact Disc (CD) and a Digital Versatile Disc (DVD) may be used as the memory 24.

The memory 24 stores the projection data, data of the CT image, or setting data of a general-purpose protocol, etc. The memory 24 also stores biometric information 24a of the subject P acquired by the sensor 30, and characteristic information 24b extracted from the biometric information. Furthermore, the memory 24 stores a program 24c including instructions for realizing new processing functions such as an acquisition function 28a, an extraction function 28b, and an assist function 28c of the control circuit 28.

The control circuit 28 reads out the program 24c stored in the memory 24, expands it in a memory 24, and controls each of the units in accordance with the expanded program 24c. The control circuit 28 comprises the acquisition function 28a, the extraction function 28b, and the assist function 28c as the new processing functions according to the embodiment.

In other words, a control program includes, in addition to a code for making the computer 20 function as the memory 24, codes for making the computer 20 function as an acquisition unit having the acquisition function 28a, function as an extraction unit having the extraction function 28b, and function as an assist unit having the assist function 28c.

The acquisition function 28a acquires from the sensor 30 at least the biometric information 24a of the subject P acquired while the imaging is in progress by the scanner 10 of the X-ray CT scanner. "Imaging in progress" does not indicate only a time when the X-ray is irradiated. From the time the subject P enters an X-ray imaging room to until the time the subject leaves, when the subject P is lying down on the patient table, or a state where the top plate 14 slides and places the subject P inside the gantry may also be referred to as "imaging in progress."

The extraction function 28b processes the biometric information 24a acquired during imaging by the scanner 10 of the X-ray CT scanner, and extracts the characteristic information of the subject P. The extracted characteristic information is associated with the subject P and is stored in the memory 24 (characteristic information 24b).

The characteristic information is, for example, information that the amount of perspiration has increased, the heart rate has increased, respiration was not paused sufficiently when required, or the body temperature has increased or decreased, which is caused by increased stress due to entering the gantry. In some cases, such characteristic information indicates, for example, psychological tendencies of the subject P. In addition, characteristic information may also include information indicating tendencies of body motion such as the posture changing unintentionally with the movement of the top plate 14. The body motion may be sensed by, for example, an image sensor. The body motion may also be detected from a change in the subject in an image photographed in a time series.

The characteristic information may be understood as information that is stored, for example, by associating the protocol of image capture (type of image capture) with a change in biometric information of the subject.

For example, the amount of perspiration sensed by a perspiration sensor is an example of the biometric information. Information that the amount of perspiration has exceeded a predetermined value during image capture would be fed back to the next study (imaging) as the characteristic information of the subject.

A heart rate sensed by an ECG (a heartbeat sensor) is also an example of the biometric information. Information that the heart rate has exceeded a preset value during image capture, the level of heart rate variation has exceeded a preset value during image capture, or the occurrence of pulsation that cannot be recognized as a normal heartbeat has exceeded a preset value, is fed back to the next study (imaging) as the characteristic information of the subject.

The temperature sensed by a body temperature sensor is also an example of the biometric information. Information that the body temperature has deviated from a predetermined range during image capture is fed back to the next study (imaging) as characteristic information of the subject.

Information sensed by a respiration sensor is also an example of the biometric information. During image capture, information that a time period of inhaling and exhaling has fallen below/risen above a predetermined normal range is fed back to the next imaging as characteristic information of the subject. Information that there was breathing during image capture in an study that requires imaging to be performed while holding a breath after inhaling (lung field CT imaging, etc.) is fed back to the next study (imaging) as characteristic information of the subject.

Information sensed by a body motion sensor is also an example of the biometric information. During image capture, information that a body motion has occurred beyond a predetermined distance is fed back to the next study (imaging) as characteristic information of the subject.

The characteristic information may be understood as a combination of the protocol and the change in biometric information. For example, in the case of performing MR imaging of a head area, information that a body motion of the head area has occurred, or, in the case of lung field CT imaging, information that breathing has occurred during image capture is recorded as the characteristic information of the subject.

Furthermore, it is also possible to include in the characteristic information a lapse of time from a time at which an event in the protocol has occurred.

For example, in the case of contrast CT imaging, information that a body motion has occurred after two minutes of injecting a contrast agent is also one of the characteristic information.

For example, characteristic information unique to each subject can be extracted by associating the acquired biometric information with a time stamp or a subject ID and filtering it. Roughly, a matter such as distinguishing likes/dislikes of CT imaging, or information on the tendency of body motion occurrence after a few minutes of injecting a contrast agent, and the tendency of a body part, such as the head, among the areas of a body for body motion to occur more in comparison to the other areas, etc. may also be considered as one of the characteristic information.

In particular, the extraction function 28b extracts the characteristic information 24b of the subject P based on the biometric information 24a accumulated in the memory 24, or the server 1 or the database DB of the cloud CL.

The extraction function 28b may also extract the characteristic information of the subject P based on the cause-effect relationship between the protocol applied to the subject P up until the previous study, and medical image data acquired based on this applied protocol. In other words, if an image (artifact) indicating body motion is recognized on the medical image data photographed based on a certain protocol, a tendency that body motion occurs easily in the protocol can be ascertained.

The assist function 28c assists the design of a protocol for the current study based on the characteristic information of the subject P acquired/collected up until the previous study.

For example, when an imaging target area of the subject P is designated by an study order, the assist function 28c may assist the design of the protocol based on the characteristic information collected up until the previous study in order to obtain a clear image for this imaging target area.

For example, the assist function 28c creates a protocol for the current study based on the extracted characteristic information. For example, the assist function 28c creates a protocol for the current study by modifying the general-purpose protocol based on the characteristic information of the subject P. By using a protocol on which the characteristic information is reflected instead of using the general-purpose protocol, imaging can be realized in consideration of the characteristics of each subject. This may enhance the quality of the medical image, which would be of use in diagnoses.

Figure 3:
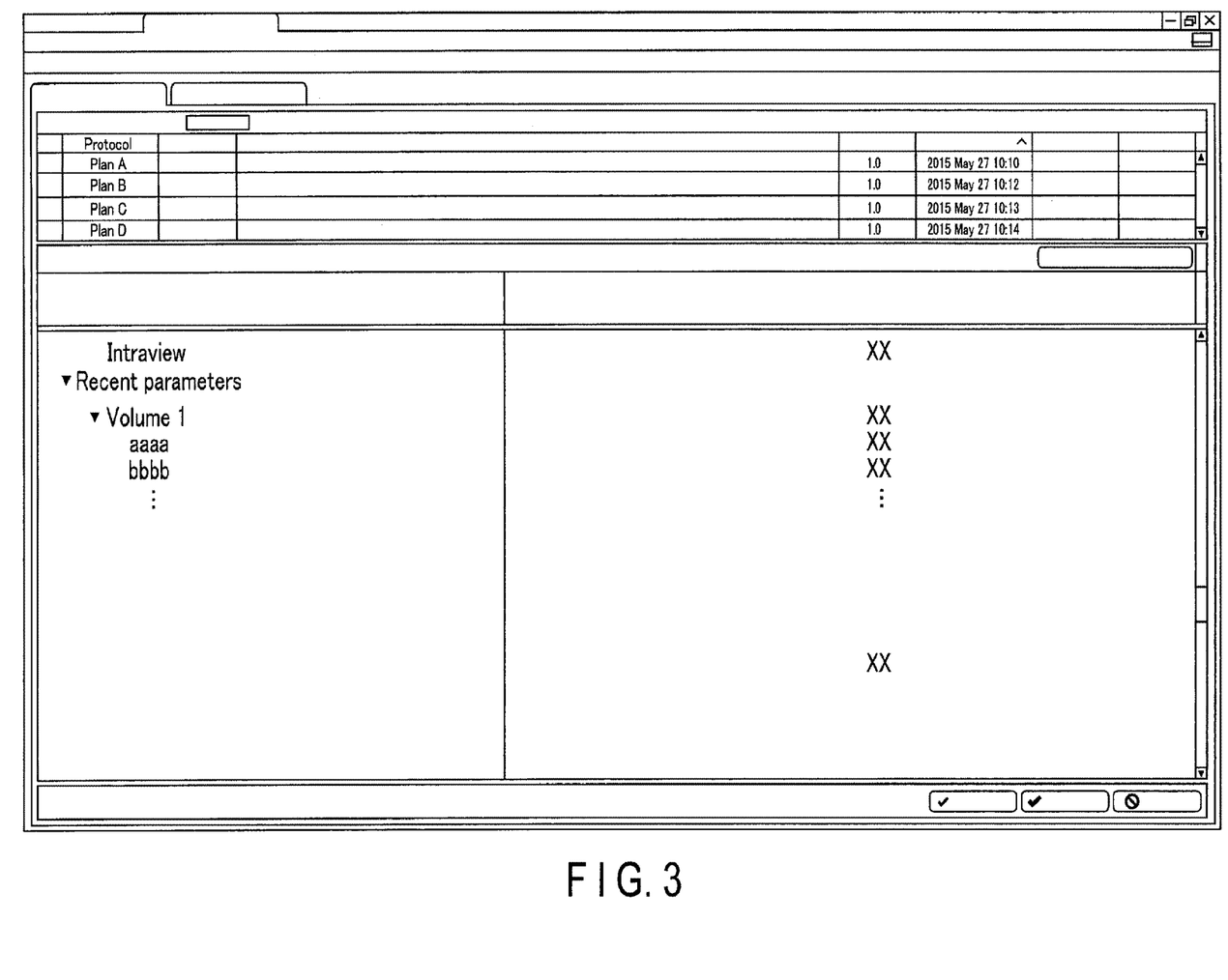
FIG. 3 shows an example of a graphical user interface (GUI) window concerning an operation of the modality 3.

The created protocol can be displayed in the GUI window shown, for example, in FIG. 3. FIG. 3 shows an example of the GUI window concerning an operation of the modality 3. The operator operates the modality 3 in accordance with the content displayed in the window. At this time, in the embodiment, the characteristic information of the subject P is displayed in this window.

On the basis of the above configuration, a plurality of embodiments will be explained in the following.

First Embodiment

Figure 4:
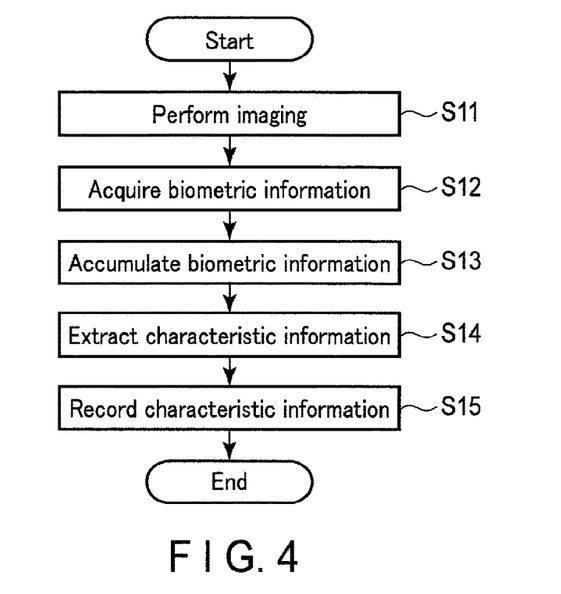
FIG. 4 is a flowchart showing an example of processing procedures of the modality 3 shown in FIG. 2.

FIG. 4 is a flowchart showing an example of a processing procedure of the modality 3 shown in FIG. 2. This flowchart shows the processing procedure performed by the modality 3 while the subject P is being photographed. In FIG. 4, when X-ray imaging of the subject P is started (step S11), the modality 3 (X-ray CT scanner) acquires biometric information from the sensor 30 simultaneously and in parallel with the imaging (step S12). The acquired biometric information is accumulated in the memory 24 or the database DB (step S14). When the imaging is ended, the modality 3 extracts the characteristic information of the subject P from the biometric information (step S14). The extracted characteristic information is associated with the subject ID and recorded in the memory 24 or the database DB (step S15).

Figure 5:
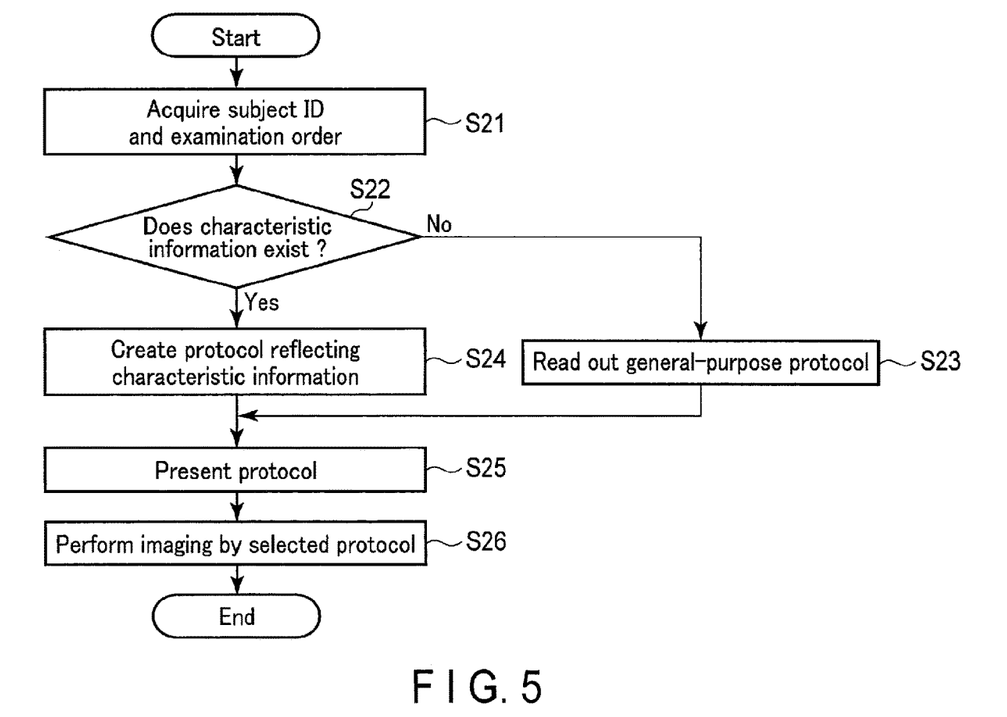
FIG. 5 is a flowchart showing another example of processing procedures of the modality 3 shown in FIG. 2.

FIG. 5 is a flowchart showing another example of a processing procedure of the modality 3 shown in FIG. 2. When an imaging flow is started, for example, a doctor using a hospital information management system (HIS) provides an study order (instruction) in which a subject ID is designated to the modality 3 (step S21). The modality 3 then searches the memory 24 or the database DB to determine whether or not characteristic information of the designated subject exists (step S22).

If the characteristic information does not exist (No), the modality 3 reads out from the memory 24 a general-purpose protocol in accordance with general characteristics (age, sex, etc.) of the subject P based on the study order (step S23). The read out protocol is displayed in, for example, a form of a list in the GUI window of the display 22 and is presented to an operator (radiology technician, etc.) of the modality 3 (step S25).

On the other hand, if the characteristic information extracted in the past is found in step S22 (Yes), the assist function 28c of the control circuit 28 revises the protocol which is based on the study order in accordance with the characteristic information, and creates a protocol that reflects the characteristic information of the subject P (step S24). The created protocol is displayed in, for example, a form of a list in the GUI window of the display 22 and is presented to the operator (radiology technician, etc.) of the modality 3 (step S25).

The operator selects one protocol from the presented protocols. The scan controller 21 of the modality 3 then controls the scanner 10 in accordance with the selected protocol, and starts imaging the subject P (step S26).

At a clinical site, the following examples may be considered. For example, when a data set of an order such as "perform CT imaging of the lung field to confirm a nodule of the lung field" and a subject ID is given, an operator selects a protocol based on the order. If characteristic information of the subject does not exist, the operator selects an appropriate protocol from a group of regular protocols.

On the other hand, if the characteristic information of the subject exists, the modality 3 revises the general-purpose protocol in accordance with the characteristic information, or creates a new protocol. The operator can select an appropriate protocol from the group of protocols prepared in accordance with the characteristic information.

Generally, in the case of performing helical scanning with respect to the lung field, it is necessary to hold a breath throughout the helical scanning. A group of default protocols corresponding to the order such as "perform CT imaging of the lung field to confirm a nodule of the lung field" includes a protocol of the helical scanning to the lung field. However, in the case where the characteristic information of the subject of the imaging target is such that "breathing occurred while imaging lung field (failed to hold breath)," it is preferred to not use the helical scanning protocol. Therefore, in the embodiment, a step and shoot protocol is created as a protocol for the current study and presented to an operator.

As mentioned above, in the first embodiment, the biometric information of the subject P is recorded/accumulated during imaging, and the characteristic information such as the change in heart rate and the change in respiration that occurred during scanning are extracted for each subject from the biometric information. The extracted characteristic information may be stored in the modality 3, may be recorded in the server 1 via the LAN 5 of the hospital system 100, or may be accumulated in the database DB of the cloud CL. When performing the next study for the subject, if the characteristic information of the corresponding subject exists, a protocol reflecting such characteristic information is created and used.

The existing techniques are not capable of designing a protocol in accordance with the characteristics of each subject. Therefore, events such as the rise in heart rate that occurred during the previous imaging, and exhaling during imaging were unable to be used as a finding for the next study. Therefore, not only was imaging troublesome due to re-takes, but also would have caused radiation exposure to increase.

In contrast, in the first embodiment, the change in heart rate and the change in respiration that occurred during scanning are extracted from the biometric information such as that of an electrocardiogram or a respirometry recorded during imaging, and are stored in the system as the characteristic information for each subject. When the same subject is currently being examined, a protocol is created based on the characteristic information and applied.

This allows the findings obtained in each imaging to be fed back to the next imaging, which would allow the subject to be photographed more intelligently. Furthermore, this will allow study efficiency to improve and cause less stress on the subject (patient). Therefore, according to the first embodiment, a medical image diagnosis apparatus, a server, and a control method which allow the characteristics of the subject to be reflected in the protocol can be provided.

Second Embodiment

Figure 6:
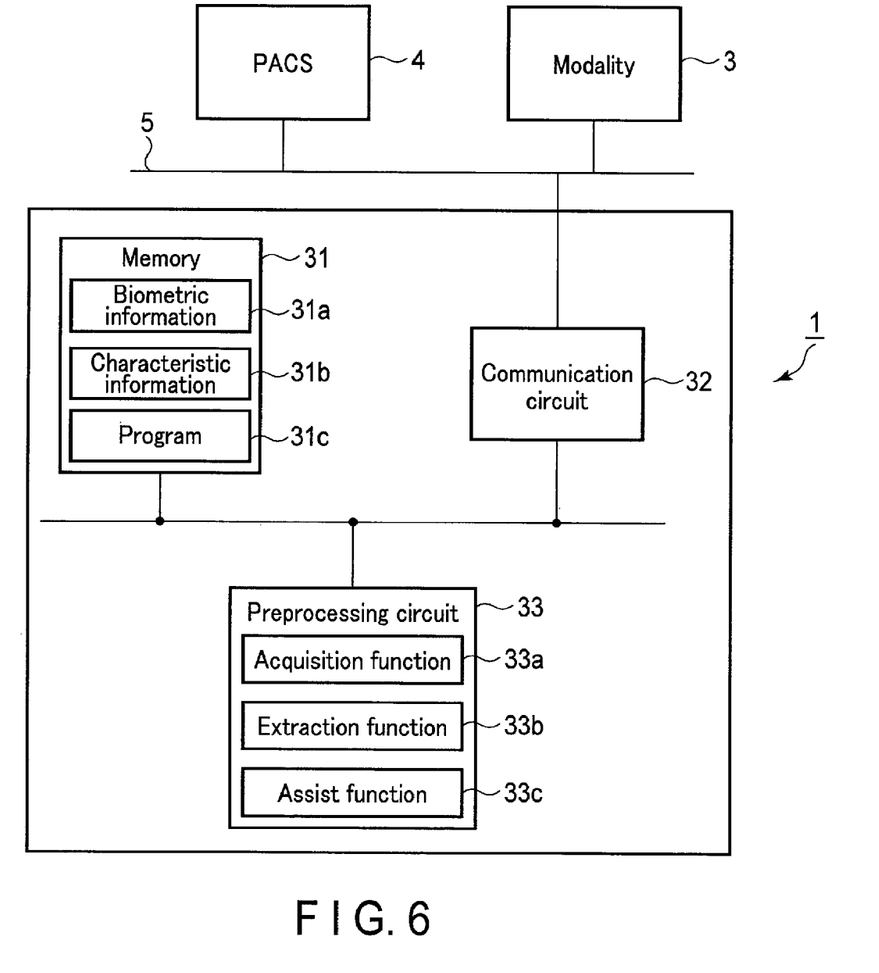
FIG. 6 is a functional block diagram showing an example of a server 1.

FIG. 6 is a function block diagram showing an example of the server 1. The server 1 comprises a memory 31, a communication circuit 32, and a processing circuit 33. The communication circuit 32 is connected to the LAN 5 and functions as an interface for communicating with PACS 4 and the modality 3.

The memory 31 stores the biometric information (31a), the characteristic information (31b), and the program (31c) explained in the first embodiment. The processing circuit 33 comprises an acquisition function 33a, an extraction function 33b, and an assist function 33c.

The program 31c includes codes for making the server 1 serving as a computer, function as an acquisition unit having the acquisition function 31c, an extraction unit having the extraction function 33b, and an assist unit having the assist function 33c. The acquisition function 33a, the extraction function 33b, and the assist function 33c each have the same function as the acquisition function 29a, the extraction function 28b, and the assist function 28c mentioned in the first embodiment. In other words, the second embodiment corresponds to a configuration in which the server 1 has the function of the computer 20 shown in FIG. 2.

Figure 7:
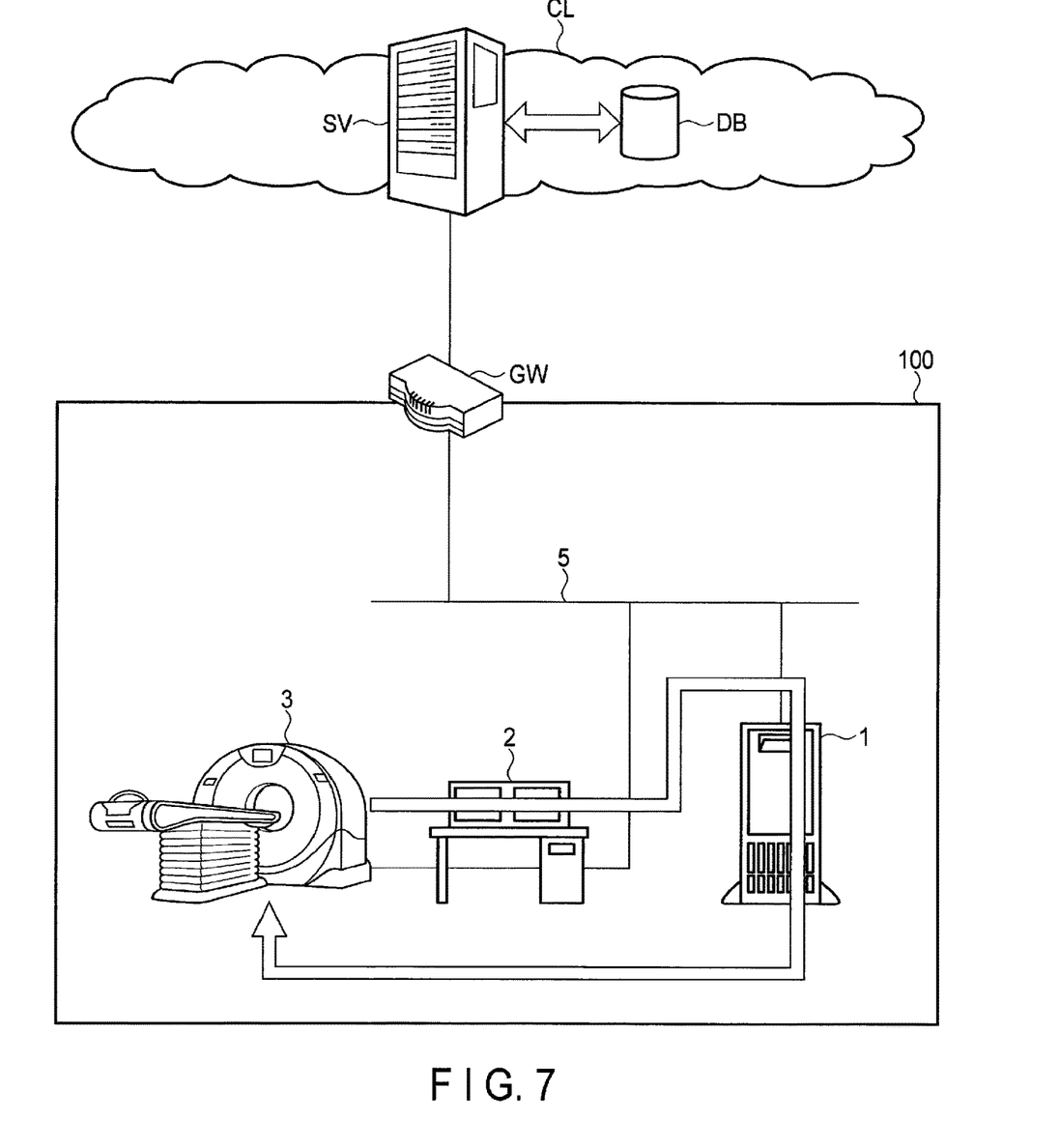
FIG. 7 is a diagram schematically showing a flow of information in a second embodiment.

FIG. 7 is a diagram schematically showing a flow of information in the second embodiment. In FIG. 7, the biometric information acquired during imaging using the modality 3 is sent to the server 1 via the console 2. The server 1 extracts the characteristic information of the subject P in the same procedure as that explained in the first embodiment. The extracted characteristic information is used for the next and subsequent imaging by the modality 3.

The above configuration can also produce the same effect as the first embodiment. In addition, in the second embodiment, since a resource required for calculation is established outside the modality 3, it produces an effect that the configuration of the modality 3 may, therefore, be simplified.

Third Embodiment

Figure 8:
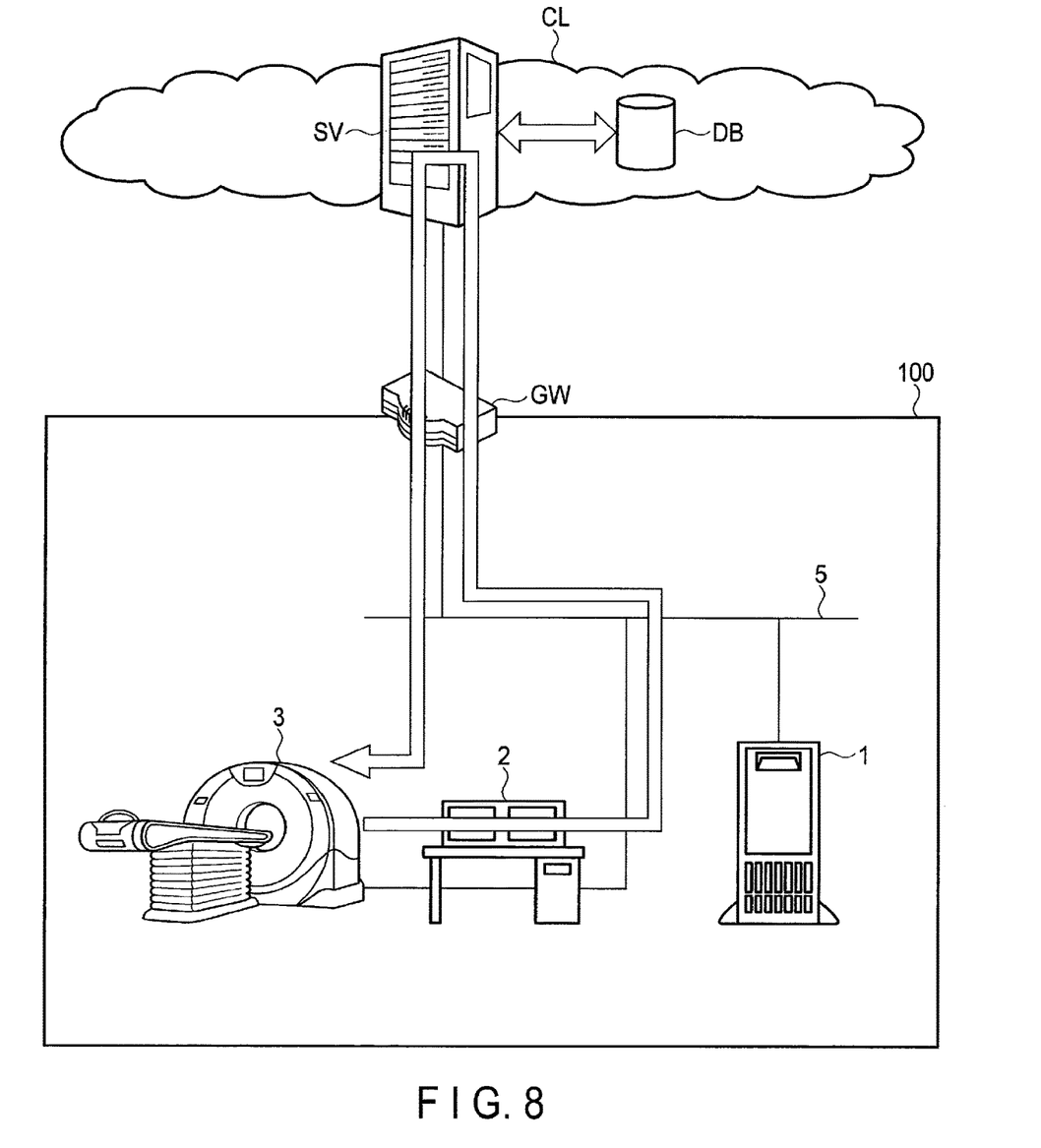
FIG. 8 is a diagram schematically showing a flow of information in a third embodiment.

FIG. 8 is a diagram schematically showing a flow of information in a third embodiment. In FIG. 8, the biometric information acquired during imaging using the modality 3 is sent from the console 2 to the server SV of the cloud CL via the gateway GW. The server SV comprises the same function as the server 1 shown in FIG. 6, accumulates the acquired biometric information in the database DB, and calculates the characteristic information of the subject in the same procedure as in the flowchart shown in FIG. 4.

Prior to the imaging using the modality 3, the server SV prepares a protocol in the same procedure as set forth in the flowchart shown in FIG. 5, and notifies this protocol to the console 2 via the gateway GW. The modality 3 starts imaging the subject P in accordance with the notified protocol.

According to such configuration, it would be possible to share the characteristic information of the same subject between a plurality of hospitals. Furthermore, since computing capabilities of the cloud CL can be used, an advantage such as improved throughput may be obtained.

Fourth Embodiment

Figure 9:
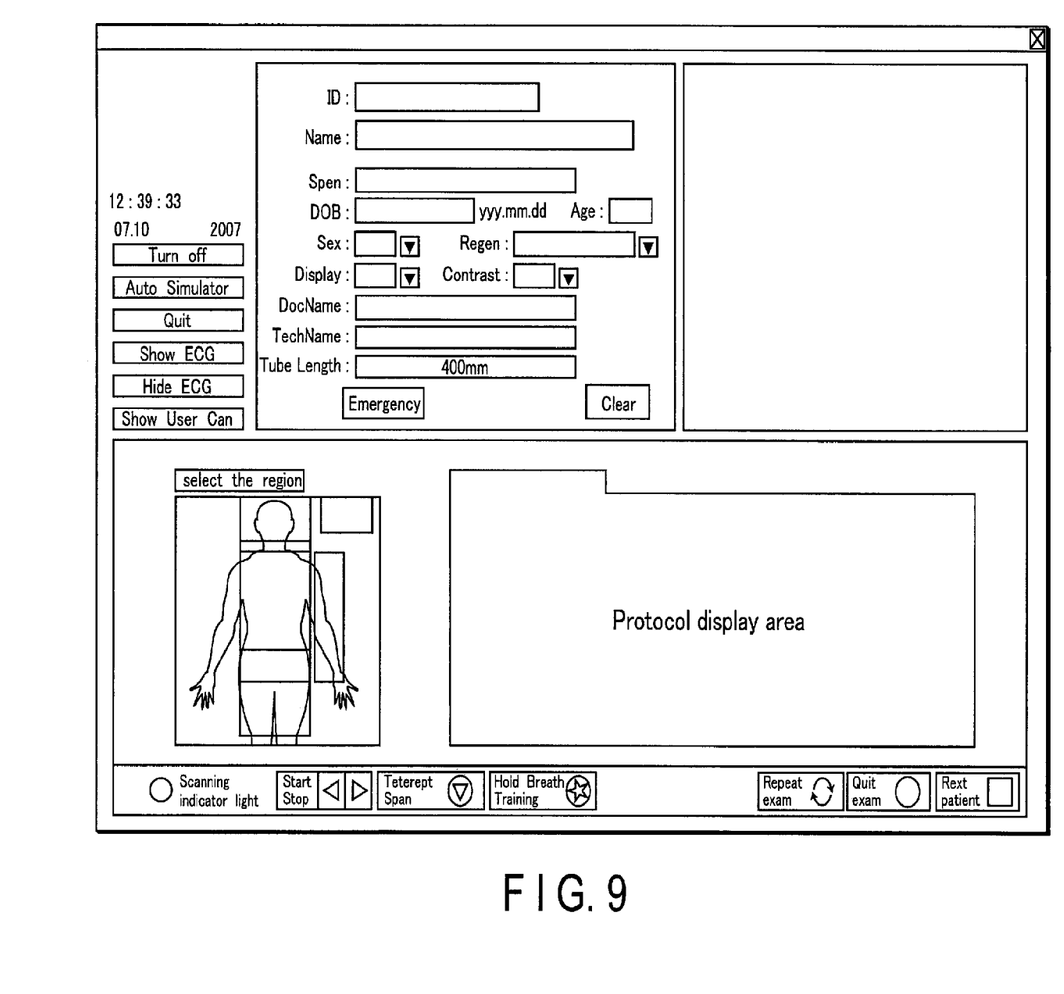
FIG. 9 shows another example of a GUI window concerning an operation of the modality 3.

FIG. 9 shows another example of a GUI window concerning an operation of the modality 3. FIG. 9 shows an example of a GUI screen displayed, for example, in a scanning plan creation utility software. This window is displayed on, for example, a display of the console 2 (FIG. 1).

Various types of information related to imaging by the modality 3 is displayed in the window. For example, patient information (ID, name, etc.) of the subject of the study target, a region to be photographed by the modality 3, and a main menu are displayed in the window. Furthermore, this window comprises an area for displaying a protocol related to the current study (protocol display area).

In the first embodiment, the protocol for the current study is created based on the characteristic information acquired up until the previous study. In the fourth embodiment, a protocol that should not be applied in the current study (inappropriate protocol) is identified based on the characteristic information acquired up until the previous study, and the result thereof is presented to the operator.

In the fourth embodiment, the assist function 28c identifies an inappropriate protocol to be removed based on the extracted characteristic information of the subject P. The assist function 28c displays the identified inappropriate protocol in a console window by distinguishing it from the other protocols.

Figure 10:
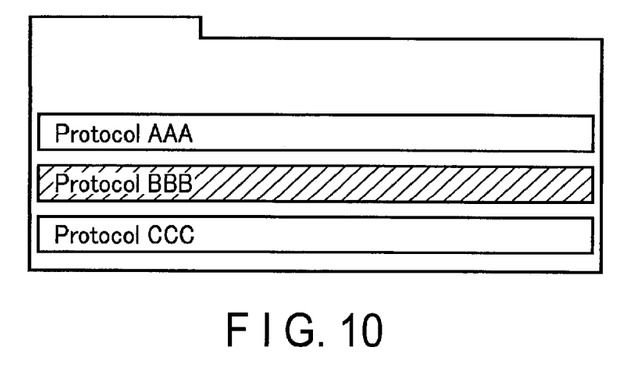
FIG. 10 shows an example of distinguishably displaying an inappropriate protocol and an appropriate protocol in a protocol display area.

FIG. 10 shows an example of displaying an inappropriate protocol and an appropriate protocol distinguishably in a protocol display area. Among the protocols shown in FIG. 10, protocols AAA and CCC are protocols applicable to the current study, which, therefore, can be designated by clicking one of them in the window by a mouse. Meanwhile, protocol BBB is the identified inappropriate protocol, which is highlighted and distinguished from the protocols AAA and CCC, and cannot be selected even by clicking.

Therefore, in the fourth embodiment, a protocol which should not be applied (inappropriate protocol) is identified based on the characteristic information of the subject, and is highlighted and displayed in the GUI window. Also, the characteristic information of the subject obtained up until the previous study can be used as a finding in the latest study, and can be used to improve the quality of the study.

Fifth Embodiment

In the fifth embodiment, inappropriate protocols are identified, and protocols are narrowed down to protocols that are applicable to the subject based on such result.

In the fifth embodiment, the assist function 28c identifies inappropriate protocols that should be removed based on the extracted characteristic information of the subject P. Based on the inappropriate protocols that are identified, the assist function 28c narrows down the applicable protocols from among a plurality of protocols and displays the result thereof in the GUI window.

Figure 11:
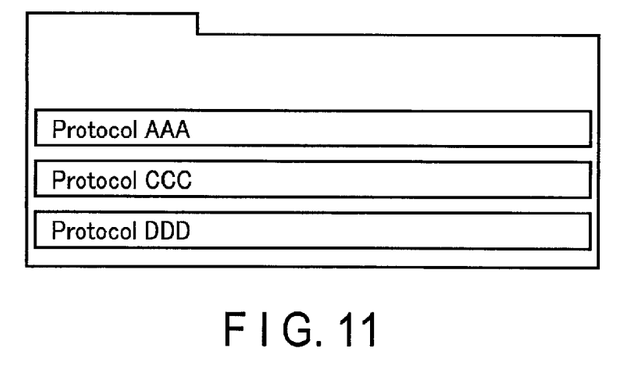
FIG. 11 shows an example of displaying a narrowed down protocol as an applicable protocol.

FIG. 11 shows an example of displaying the narrowed down protocols as applicable protocols. Protocols AAA, CCC, and DDD shown in FIG. 11 are protocols applicable to the current study, and can all be designated by clicking with a mouse.

Furthermore, based on a given index, the order in which the protocols are displayed may be changed. For instance, when the protocols AAA, CCC, and DDD are evaluated based on an index such as radiation exposure, a result such as protocols CCC<AAA<DDD in ascending order of radiation exposure may be obtained. The protocol CCC may be arranged at the most noticeable position (the very top) in the window, in the order of CCC, AAA, and DDD from the top. As other examples, applicable protocols may be evaluated based on appropriate indexes such as imaging time, and displayed in an order reflecting the result.

Therefore, in the fifth embodiment, protocols that should not be applied (inappropriate protocols) are identified based on the characteristic information of the subject, and only the applicable protocols narrowed down based on the result thereof are displayed in the GUI window. Also, the characteristic information of the subject obtained up until the previous study can be used as a finding in the latest study, and can be used to improve the quality of the study.

This invention is not limited to the above embodiments.

For example, in the first embodiment, it has been explained that a protocol reflecting the characteristic information of the subject P is created, and that this protocol is applied in the next study for imaging. Other than this, it may be such that the created protocol is only suggested in the GUI window, and the operator is entrusted with the decision on whether or not to apply the protocol to the actual imaging. Alternatively, the characteristic information may only be displayed in the GUI window as supplementary information. For example, the fact that "in the previous study, heart rate increased more than normal" may be identified by the assist function 28c based on the subject ID, and may only be displayed on the display 22. For example, when the assist function 28c recognizes that the biometric information (change in heart rate or respiration frequency) exceeds a predetermined threshold value by a given rate, it identifies that such fact has occurred. This will allow the operator to set a more suitable protocol by referring to the displayed information.

In the embodiment, the finding obtained by the X-ray CT scanner has been made available to the next imaging performed by the X-ray CT scanner. In addition, the characteristic information obtained by the X-ray CT scanner may, for example, also be made available when performing imaging by an MRI device. In other words, the finding obtained by a second modality may be used to create a protocol when imaging is performed by the second modality. Information sharing between modalities in this manner has high compatibility with a configuration that utilizes the service of the cloud CL, particularly as in the third embodiment.

In the embodiment, an IaaS-type service which provides resources such as a sever device, a central processing unit and a storage as a service (public cloud) has been assumed. Instead of the above, it is also possible to utilize a cloud which is a Software as a Service (SaaS) type that provides applications (software) as a service, or a Platform as a Service (PaaS) type that provides a basis (platform) for activating an application as a service.

Furthermore, each function of the preprocessing circuit 26, the reconstruction circuit 27, the scan controller 21, the display 22, and the operating circuit 23 in FIG. 2 may, for example, be stored in the memory 24 in a form of a program executable by the control circuit 28. The control circuit 28 comprises a processor that reads out a program from a memory 24 and executes it to realize a function corresponding to each program. That is, the control circuit 28 that has readout each program would comprise each of the functions shown in the computer 20 of FIG. 2.

Instead of storing the program in the memory, it is also possible to incorporate the program directly into the circuit of the processor. In this type of configuration, a processor realizes a function by reading out and executing the program incorporated in the circuit.

FIG. 2 exemplifies a single computer 20 realizing functions such as an acquisition function 28a, an extraction function 28b and an assist function 28c by a single processor (control circuit 28). FIG. 2 exemplifies a single computer 20 realizing functions such as a preprocessing circuit 26, a reconstruction circuit 27, a scan controller 21 and an operating circuit 23 by a single processor. Instead of the above, a plurality of independent processors may be combined to configure a processing circuit, in which each processor realizes each function by executing a program.

The term "processor" used in the above explanations indicates, for example, a central processing unit (CPU), a Graphics Processing Unit (GPU), or circuits such as an Application Specific Integrated Circuit (ASIC), a Programmable Logic Device (for example, a Simple Programmable Logic Device (SPLD), a Complex Programmable Logic Device (CPLD), or a Field Programmable Gate Array (FPGA)).

While certain embodiments have been described, these embodiments have been presented by way of example only, and are not intended to limit the scope. Indeed, the novel embodiments described herein may be embodied in a variety of other forms; furthermore, various omissions, substitutions and changes in the form of the embodiments described herein may be made without departing from the spirit. The accompanying claims and their equivalents are intended to cover such forms or modifications as would fall within the scope and spirit.

The invention claimed is:

1. A medical image diagnosis apparatus which is accessible to an external medical scanner, the medical image diagnosis apparatus comprising:
   processing circuitry configured to:
      acquire, from the medical scanner, medical image data obtained by imaging a subject based on a protocol, which is a predetermined imaging procedure;
      extract characteristic information of the subject based on a cause-effect relationship as a combination of the protocol and abnormal biometric information of the subject acquired by a sensor at a same time as an imaging scan in a previous study using the medical scanner, the abnormal biometric information indicating that a measurement value relating to biometric information sensed by the sensor changed in a previous study such that the measurement value fell outside a normal range in the previous study; and
      automatically determine whether a protocol for a current study is appropriate or not by using the extracted characteristic information of the subject.

2. The medical image diagnosis apparatus of claim 1, wherein the processing circuitry is further configured to
   create the protocol for the current study based on the extracted characteristic information; and
   present the created protocol.

3. The medical image diagnosis apparatus of claim 1, wherein the processing circuitry is further configured to
   identify an inappropriate protocol that should be removed based on the extracted characteristic information; and
   present the identified inappropriate protocol by distinguishing the identified inappropriate protocol from other protocols.

4. The medical image diagnosis apparatus of claim 1, wherein the processing circuitry is further configured to
   identify an inappropriate protocol that should be removed based on the extracted characteristic information;
   narrow down protocols to a protocol applicable to the subject based on the identified inappropriate protocol; and
   present the applicable protocol.

5. The medical image diagnosis apparatus of claim 1, wherein the processing circuitry is further configured to assist a design of the protocol based on a designated imaging target area of the subject.

6. The medical image diagnosis apparatus of claim 1, further comprising a memory, and
wherein the processing circuitry is further configured to
associate the extracted characteristic information with the subject; and
store the characteristic information associated with the subject in the memory.

7. The medical image diagnosis apparatus of claim 1, wherein the processing circuitry is further configured to
accumulate the acquired abnormal biometric information in a database via a network; and
extract the characteristic information based on the accumulated abnormal biometric information.

8. The medical image diagnosis apparatus of claim 1, wherein the processing circuitry is further configured to acquire the abnormal biometric information, which is at least one of a heart rate, respiration information, a body temperature, and an amount of perspiration.

9. The medical image diagnosis apparatus of claim 1, wherein the characteristic information is information indicating a tendency of a body motion of the subject.

10. The medical image diagnosis apparatus of claim 1, wherein the processing circuitry is further configured to
extract the characteristic information of the subject based on the cause-and-effect relationship between the protocol applied to the subject up to and including the previous study, and previous medical image data acquired based on the applied protocol.

11. A server configured to communicate with a medical image diagnosis apparatus that acquires, from an external medical scanner, medical image data obtained by imaging a subject based on a protocol, which is a predetermined imaging procedure, the server comprising:
processing circuitry configured to:
extract characteristic information of the subject based on a cause-effect relationship as a combination of the protocol and abnormal biometric information of the subject acquired by a sensor at a same time as an imaging scan in a previous study using the medical scanner, the abnormal biometric information indicating that a measurement value relating to biometric information sensed by the sensor changed in a previous study such that the measurement value fell outside a normal range in the previous study; and
automatically determine whether a protocol for a current study is appropriate or not by using the extracted characteristic information of the subject.

12. The server of claim 11, wherein the processing circuitry is further configured to
create the protocol for the current study based on the extracted characteristic information; and
present the created protocol.

13. The server of claim 11, wherein the processing circuitry is further configured to
identify an inappropriate protocol that should be removed based on the extracted characteristic information; and
present the identified inappropriate protocol by distinguishing the identified inappropriate protocol from other protocols.

14. The server of claim 11, wherein the processing circuitry is further configured to
identify an inappropriate protocol that should be removed based on the extracted characteristic information;
narrow down protocols to a protocol applicable to the subject based on the identified inappropriate protocol; and
present the applicable protocol.

15. The server of claim 11, wherein the processing circuitry is further configured to assist a design of the protocol based on a designated imaging target area of the subject.

16. The server of claim 11, further comprising a memory, and
wherein the processing circuitry is further configured to
associate the extracted characteristic information with the subject; and
store the characteristic information associated with the subject in the memory.

17. The server of claim 11, wherein the processing circuitry is further configured to
accumulate the acquired abnormal biometric information in a database via a network; and
extract the characteristic information based on the accumulated abnormal biometric information.

18. The server of claim 11, wherein the processing circuitry is further configured to acquire the abnormal biometric information, which is at least one of a heart rate, respiration information, a body temperature, and an amount of perspiration.

19. The server of claim 11, wherein the characteristic information is information indicating a tendency of a body motion of the subject.

20. A control method for controlling, by a computer, a medical image diagnosis apparatus that acquires, from an external medical scanner, medical image data obtained by imaging a subject based on a protocol, which is a predetermined imaging procedure, the method comprising:
the computer extracting characteristic information of the subject based on cause-effect relationship as combination of the protocol and abnormal biometric information of the subject acquired by a sensor at a same time as an imaging scan in a previous study using the medical scanner, the abnormal biometric information indicating that a measurement value relating to biometric information sensed by the sensor changed in a previous study such that the measurement value fell outside a normal range in the previous study; and
the computer automatically determining whether a protocol for a current study is appropriate or not by using the extracted characteristic information of the subject.

* * * * *